US010369085B2

(12) United States Patent
Kennard et al.

(10) Patent No.: US 10,369,085 B2
(45) Date of Patent: *Aug. 6, 2019

(54) RESIN REINFORCED ZINC POLYCARBOXYLATE TEMPORARY CEMENT COMPOSITIONS AND RELATED KITS

(71) Applicant: ULTRADENT PRODUCTS INC., South Jordan, UT (US)

(72) Inventors: Gordon Kennard, Cedar Hills, UT (US); Andy T. Kawamoto, Sandy, UT (US); Jeff Wagner, Sandy, UT (US)

(73) Assignee: ULTRADENT PRODUCTS, INC., South Jordan, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/883,383

(22) Filed: Jan. 30, 2018

(65) Prior Publication Data

US 2018/0153775 A1 Jun. 7, 2018

Related U.S. Application Data

(63) Continuation of application No. 15/377,470, filed on Dec. 13, 2016, now Pat. No. 9,907,732, which is a continuation of application No. 14/990,507, filed on Jan. 7, 2016, now Pat. No. 9,549,880, which is a continuation of application No. 11/680,284, filed on Feb. 28, 2007, now Pat. No. 9,289,358.

(51) Int. Cl.
| | |
|---|---|
| *A61K 6/083* | (2006.01) |
| *A61K 6/00* | (2006.01) |
| *A61C 5/30* | (2017.01) |
| *A61C 3/16* | (2006.01) |
| *A61C 13/107* | (2006.01) |
| *A61C 5/70* | (2017.01) |
| *A61C 5/64* | (2017.01) |

(52) U.S. Cl.
CPC .............. *A61K 6/0023* (2013.01); *A61C 3/16* (2013.01); *A61C 5/30* (2017.02); *A61C 5/64* (2017.02); *A61C 5/70* (2017.02); *A61C 13/0001* (2013.01); *A61K 6/0002* (2013.01); *A61K 6/005* (2013.01); *A61K 6/0073* (2013.01); *A61K 6/0835* (2013.01); *A61K 6/083* (2013.01)

(58) Field of Classification Search
CPC ..................................................... A61K 6/083
See application file for complete search history.

(56) References Cited

U.S. PATENT DOCUMENTS

| | | |
|---|---|---|
| 4,816,495 A | 3/1989 | Blackwell et al. |
| 4,886,843 A | 12/1989 | Walton |
| 5,084,491 A | 1/1992 | Kerby |
| 5,154,613 A | 10/1992 | Cohen |
| 5,218,070 A | 6/1993 | Blackwell |
| 5,338,773 A | 8/1994 | Lu et al. |
| 5,367,002 A | 11/1994 | Huang et al. |
| 5,534,562 A | 7/1996 | Jensen et al. |
| 5,708,052 A | 1/1998 | Fischer et al. |
| 5,710,194 A | 1/1998 | Hammesfahr |
| 5,886,064 A | 3/1999 | Rheinberger et al. |
| 6,133,339 A | 10/2000 | Xie et al. |
| 6,291,548 B1 | 9/2001 | Akahane et al. |
| 6,306,206 B1 | 10/2001 | Fischer et al. |
| 6,313,192 B1 | 11/2001 | Anstice et al. |
| 6,398,859 B1 | 6/2002 | Dickens et al. |
| 6,500,004 B2 | 12/2002 | Jensen et al. |
| 6,765,038 B2 | 7/2004 | Mitra |
| 6,787,629 B2 | 9/2004 | Jia et al. |
| 6,814,794 B2 | 11/2004 | Allred |
| 6,852,775 B1 | 2/2005 | Soglowek et al. |
| 6,953,832 B2 | 10/2005 | Moszner et al. |
| 6,979,702 B1 | 12/2005 | Ma et al. |
| 6,998,111 B2 | 2/2006 | Klee et al. |
| 7,090,721 B2 | 8/2006 | Craig et al. |
| 7,091,259 B2 | 8/2006 | Bui et al. |
| 7,166,651 B2 | 1/2007 | Qian |
| 9,289,358 B2 * | 3/2016 | Kennard ................... A61C 3/16 |
| 9,549,880 B2 * | 1/2017 | Kennard ................... A61C 3/16 |
| 9,907,732 B2 * | 3/2018 | Kennard ................... A61C 3/16 |
| 2003/0114554 A1 | 6/2003 | Ario et al. |
| 2003/0158288 A1 | 8/2003 | Lehmann et al. |
| 2004/0235981 A1 | 11/2004 | Qian |
| 2005/0004254 A1 | 1/2005 | De Putter et al. |
| 2005/0009946 A1 | 1/2005 | Oguri et al. |
| 2005/0014861 A1 * | 1/2005 | Qian ................... A61K 6/0017 |
| | | 523/116 |
| 2005/0020720 A1 | 1/2005 | Dickens et al. |

(Continued)

FOREIGN PATENT DOCUMENTS

| | | |
|---|---|---|
| EP | 0391619 | 12/1993 |
| GB | 1484454 | 8/1973 |
| WO | 9312759 | 7/1993 |

OTHER PUBLICATIONS

Ruse "What is a Compomer?" Journal of the Canadian Dental Association, Oct. 1999, vol. 65, No. 9, pp. 500-504.

*Primary Examiner* — Michael F Pepitone
(74) *Attorney, Agent, or Firm* — Workman Nydegger

(57) ABSTRACT

Dental cement compositions (including two-part compositions), kits, and related methods are used for bonding a dental prosthetic appliance to a tooth. A first part includes an amine activator component and a zinc oxide reactive filler, while a second part includes a polymerization initiator (e.g., benzoyl peroxide) and a polymerizable component having a structure including at least one acrylate or methacrylate group at one end and a carboxylic acid group at another end. A temporary cement composition advantageously exhibits reduced compressive and/or bonding strength relative to permanent cement compositions, which provides sufficient strength to facilitate normal use of the teeth while the provisional appliance is in use, while also facilitating easy removal of the provisional appliance for replacement with a permanent appliance at a later time.

22 Claims, 4 Drawing Sheets

(56) References Cited

U.S. PATENT DOCUMENTS

2006/0035997 A1   2/2006  Orlowski et al.
2006/0058414 A1   3/2006  Arthur et al.
2007/0049656 A1*  3/2007  Jia .......................... A61K 6/083
                                                    523/116

* cited by examiner

RESIN REINFORCED ZINC POLYCARBOXYLATE TEMPORARY CEMENT COMPOSITIONS AND RELATED KITS

CROSS REFERENCE TO RELATED APPLICATION

This Application is a continuation of U.S. application Ser. No. 15/377,470, filed Dec. 13, 2016, now issued U.S. Pat. No. 9,907,732, which is a continuation of U.S. application Ser. No. 14/990,507, filed Jan. 7, 2016, now issued U.S. Pat. No. 9,549,880, which is a continuation of U.S. application Ser. No. 11/680,284, filed Feb. 28, 2007, now issued U.S. Pat. No. 9,289,358, the disclosures of which are incorporated herein by reference in their entirety.

BACKGROUND OF THE INVENTION

1. The Field of the Invention

The present invention relates to dental restorations. More particularly, the invention relates to temporary cement compositions and related kits and methods for temporarily bonding provisional dental restorative appliances.

2. The Relevant Technology

When a dental practitioner performs a procedure requiring the removal of a tooth or portion of a tooth, it is desirable to replace the tooth or tooth portion with a dental restorative appliance (e.g., a crown or bridge). Because permanent appliances typically take up to several weeks to prepare, the practitioner will sometimes fit a provisional appliance to replace the person's tooth until a permanent appliance is ready. The provisional appliance is intended to be a temporary prosthesis until a permanent appliance can be ordered and fabricated.

Because the provisional appliance is only intended for temporary use, it would be an improvement in the art to provide a cement composition and related kits and methods that are specifically configured for temporarily bonding a provisional appliance in place. Such a temporary cement would provide sufficient compressive strength and bonding strength to allow the patient to engage in typical use of their teeth (e.g., biting, chewing, etc.) while also having sufficiently low bonding strength characteristics so as to facilitate easily removal of the provisional appliance by the practitioner when it is desired to replace the provisional appliance with a permanent appliance.

BRIEF SUMMARY OF THE INVENTION

The present invention is directed to two-part resin-reinforced cement compositions, kits, and related methods for bonding a dental prosthetic appliance to a tooth. A first part includes an amine activator component and a zinc oxide filler, while a second part includes a polymerization initiator (e.g., benzoyl peroxide) and a polymerizable component having a structure including at least one acrylate or methacrylate group at one end and a carboxylic acid group at another end. Such a molecule may have a linear structure so as to have just two ends, or it may be branched, so as to have more than just two ends. The two parts are initially separate and then mixed together when it is desired to perform the temporary bonding. Upon mixing the components together, the amine component destabilizes the initiator, initiating curing of the polymerizable component. The zinc oxide filler reacts with the carboxylic acid group of the polymerizable component to further cure the polycarboxylate temporary cement composition.

In one embodiment, the cement is a temporary cement composition used for temporarily bonding a provisional dental prosthetic appliance to a tooth. Such a temporary cement is advantageously relatively weak so as to allow easy removal of a provisional prosthetic and the composition. In one embodiment, the bonding strength and/or compressive strength is reduced to a desirable level by inclusion of a plasticizer and/or an un-reactive filler. In one example, a plasticizer is included so as to comprise between about 15% and about 70% by weight of the composition, more preferably between about 25% and about 60% by weight of the composition, and most preferably between about 30% and about 40%) by weight of the composition. In examples including an un-reactive filler, the un-reactive filler is preferably included so as to comprise between about 3% and about 30% by weight of the composition, more preferably between about 5% and about 25% by weight of the composition, and most preferably between about 7% and about 20% by weight of the composition. In one currently preferred embodiment, both a plasticizer and un-reactive filler are included so as to collectively comprise at least about 35%, more preferably at least about 40% by weight of the composition, which the inventors have found advantageously decreases bonding strength (and compressive strength if a plasticizer is included) of the composition as compared to a composition not including these components. For example, the plasticizer acts to reduce compressive and bonding strength as it weakens the cross-linked matrix structure of the resin reinforced zinc polycarboxylate cement, while the un-reactive filler (e.g., a ceramic) serves to reduce cost and provide a desired viscosity. The un-reactive filler may also act to increase compressive strength and/or decrease bonding strength as compared to a composition where all else is equal but without the un-reactive filler.

Contrasted with typical cement compositions, which have compressive strengths of, for example, 100 MPa or more, the inventive temporary cement compositions have a compressive strength that is typically not greater than about 70 MPa, more preferably not greater than 60 MPa, more preferably not greater than about 30 MPa, and most preferably not greater than about 20 MPa. The inventive compositions advantageously have a relatively low bonding strength not greater than about 3 MPa, more preferably not greater than about 2.5 MPa, and most preferably between about 0.2 MPa and about 2 MPa, even more preferably between about 0.2 MPa and about 1 MPa. Such reduced bonding strength advantageously allows the practitioner to easily remove the temporary cement and a provisional appliance restoration when needed (e.g., once the permanent appliance is ready for installation).

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Introduction

Figure 1A:
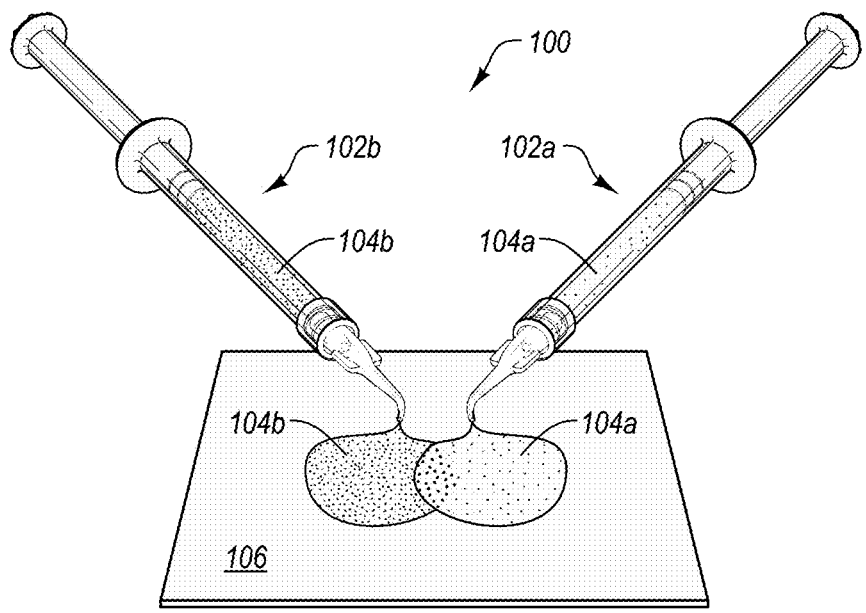
FIGS. 1A-1B illustrate exemplary systems including means for dispensing the inventive two-part temporary cement composition.

The present invention is directed to a two-part resin-reinforced cement composition and related kits and methods for bonding a dental prosthetic appliance to a tooth. The inventive composition is provided in two parts. A first part includes an amine activator component and a zinc oxide filler, while a second part includes a polymerization initiator (e.g., benzoyl peroxide) and a polymerizable component having a structure including at least one acrylate or methacrylate group at one end and a carboxylic acid group at another end. Such a molecule may have a linear structure so as to have just two ends, or it may be branched, so as to have more than just two ends. The two parts are initially separate, and are mixed together just prior to temporarily bonding the provisional restoration. Upon mixing, the amine component destabilizes the initiator, initiating curing of the polymerizable component. The zinc oxide reacts with the carboxylic acid group to further cure the polymerizable component.

II. An Exemplary Two-Part Temporary Cement Composition

The cement composition is provided in a chemical cure two-part system. A chemical cure system is advantageous as it allows the cement composition to cure even when not accessible to curing light wavelengths (i.e., it can be quite difficult to effectively light cure through a temporary crown or other provisional appliance). The first part advantageously includes an amine activator component (e.g., a tertiary amine) and a zinc oxide filler. Exemplary amine activator components include 2,2-(p-Tolylimino)diethanol (P-TIDE), a tertiary amine available from Sigma Aldrich, located in St. Louis, Mo. Other exemplary tertiary amines that may be used include, but are not limited to N,N-Dimethyl-p-toluidine (DMPT) or Ethyl 4-(Dimethylamino) Benzoate (EDMAB).

The amine activator component is preferably included in an amount ranging from about 0.01% to about 3% by weight of the composition, more preferably between about 0.05%) to about 2% by weight, and most preferably between about 0.1% and about 1% by weight of the composition.

The zinc oxide reactive filler is believed to react with the carboxylic acid group of the polymerizable component(s) within the composition so as to form a zinc polycarboxylate chelate structure. For this reason, the zinc oxide is initially separate from the polymerizable component(s) including an acrylate/methacrylate group at one end and a carboxylic acid group at another end. The total zinc oxide content (i.e., both sides together) is preferably in an amount ranging from about 3% to about 50% by weight, more preferably in an amount ranging from about 5% to about 30% by weight, and most preferably in an amount ranging from about 10% to about 20% by weight.

The second part of the two-part composition includes a polymerization initiator (e.g., a peroxide) and a polymerizable component having a structure including at least one acrylate and/or methacrylate group at one end (e.g., a HEMA group) and a carboxylic acid group at another end. The initiator (e.g., benzoyl peroxide, 2-butanone peroxide, lauroyl peroxide, tert-butyl peroxide) is preferably included in an amount ranging from about 0.01% to about 3% by weight of the composition, more preferably between about 0.05% to about 2% by weight, and most preferably between about 0.1% and about 1% by weight of the composition.

Examples of such polymerizable components include, but are not limited to mono-2-(methacryloyloxy)ethyl succinate (HEMA Succinate), available from Sigma Aldrich, located in St. Louis, Mo.; and 1,2-benzenedicarboxylic acid mono (2-((2-methyl-1-oxo-2-propenyl)oxy)ethyl) ester phthalic acid 2-hydroxyethyl ester methacrylate (also known as 2-hydroxyethylmethacrylate/phthalic anhydride, available from Esstech, located in Essington, Pa.

Mono-2-(methacryloyloxy)ethyl succinate has the structure shown below:

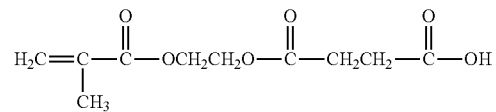

and 2-hydroxyethylmethacrylate/phthalic anhydride has the structure shown below:

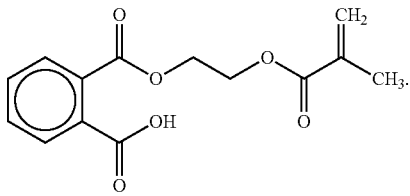

The composition may advantageously include additional polymerizable components, one or more of which may advantageously be capable of cross-linking during polymerization. Examples of such polymerizable components include various diacrylates and/or dimethacrylates, specific examples of which include bisphenol-A glycidyl methacrylate (Bis-GMA), diurethane dimethacrylate (DUDMA), triethylene glycol dimethacrylate (TEGDMA), hydroxyethyl methacrylate (HEMA) and/or glycerol di-methacrylate (GDMA). Cross-linking during polymerization results in increased overall bonding and compressive strength as compared to examples including no cross-linking polymerizable components. Because these cross-linking polymerizable components tend to have relatively high viscosities, it may be advantageous to also include one or more non-cross-linking low viscosity polymerizable components (e.g., hydroxypropylmethacrylate—HPMA) that act as thinning agents so as to reduce the overall viscosity of the part in which it is included and/or the overall composition. In addition, one or more of the polymerizable components may be phosphated so as to increase adhesion of the composition to the tooth tissue.

The composition is advantageously characterized as having relatively low bonding strength as compared to permanent bonding cements. In some embodiments, compressive strength may also be reduced as compared to permanent bonding cements. Advantageously, decreased strength (compressive and/or bonding) may be achieved through inclusion of a significant fraction of un-reactive filler and/or plasticizer within the composition. Un-reactive ceramic filler may actually increase compressive strength, while decreasing bonding strength. Plasticizers (e.g., a hydrocarbon such as polybutadiene or a polysorbate such as TWEEN-80) advantageously decrease both compressive and bonding strength.

Preferably, a temporary cement composition according to the invention has a compressive strength that is not greater than about 70 MPa, more preferably not greater than about 60 MPa, more preferably not greater than about 30 MPa, and most preferably not greater than about 20 MPa. Compressive strengths within the range of about 15-30 MPa have been found to provide sufficient strength so as to withstand chewing, biting and other forces typically encountered by a provisional dental restoration, while not being so strong as to present difficulties when replacing a provisional restoration with a permanent one.

Preferably, a temporary cement composition has a bonding strength that is not greater than about 3 MPa, more preferably not greater than about 2.5 MPa, and most preferably not greater than about 2 MPa. Bonding strengths between about 0.2 MPa and about 2 MPa, even more preferably between about 0.2 MPa and about 1 MPa have been found to provide sufficient strength so as to withstand chewing, biting and other forces typically encountered by a provisional dental restoration, while not being so strong as to present difficulties when replacing a provisional restoration with a permanent one.

Permanent cement compositions characterized by higher compressive and bonding strengths are also within the scope of the invention. In such a composition, the amount of plasticizer and/or un-reactive filler is significantly reduced, particularly the amount of any included plasticizer (which may be left out completely). Such permanent cement compositions may include a compressive strength greater than about 70 MPa, more preferably greater than about 85 MPa, and more preferably greater than about 100 MPa, and bonding strengths preferably of at least about 3 MPa, more preferably at least about 3.5 MPa, and most preferably at least about 4 MPa.

Exemplary plasticizers include, but are not limited to glycerin, HERCOLYN-D, a hydrogenated methyl ester of rosin marketed by Hercules Chemical Company, aliphatic straight chain hydrocarbons such as polybutadiene, cetyl alcohol, and/or TWEEN-80, a polysorbate. Because of their hydrophobic characteristics, an aliphatic hydrocarbon (e.g., polybutadiene) is particularly preferred as it minimizes absorption of saliva and/or water from within the mouth. Preferably any plasticizer is included in an amount ranging from about 15% to about 70% by weight of a temporary cement composition, more preferably between about 25% to about 60% by weight, and most preferably between about 30% and about 40% by weight of the temporary cement composition.

Exemplary un-reactive fillers include, but are not limited to ceramic fillers (e.g. any of various ceramic fillers sold under the trade name ZEODENT) available from J. M. Huber Corporation. Preferably any un-reactive filler is included in an amount ranging from about 3% to about 30% by weight of the composition, more preferably between about 5% to about 25% by weight, and most preferably between about 7% and about 20% by weight of the composition. In one embodiment, the strength reducing plasticizer and/or un-reactive filler collectively comprise at least about 35% by weight of the composition, more preferably at least about 40% by weight of the composition.

The second part may further advantageously include water. Water is required by the zinc oxide chelating reaction in which the zinc becomes integrated within the polycarboxylate matrix, and rather than relying on water theoretically available from saliva within the patient's mouth, the water may be directly provided within the second part of the composition. This is further advantageous as the zinc oxide reaction is believed to occur mostly after the polymerization reaction has already been completed, requiring water from saliva to diffuse through the polymerized material in order to participate in the zinc oxide reaction, which can weaken the strength of the polymerization bonds, and/or which can result in an insufficient quantity of water being made available for the reaction. Including water within the composition avoids these disadvantages by shortening overall curing time and improving efficiency and reliability of the cement composition. Water may be included within a range of about 0.05% to about 5% by weight of the composition, more preferably about 0.1%) to about 2% by weight, and most preferably about 0.15% to about 0.5% by weight of the composition.

Additional components, for example, a rheology modifying component (e.g., fumed silica), colorants, flavorants, inhibitors (e.g., BHT), and other components may additionally be included. The inclusion of a colorant (e.g., a dye or pigment) within one or both parts (e.g., yellow within part 1 and blue within part 2) so as to give each part a color different from the other part is advantageous as it provides a visual indicator that the two parts have been homogeneously mixed together. Examples of suitable pigments include Suncroma yellow iron oxide, available from Sun Chemical located in Parsippany, N.J.; V-9117 deep tan, V-9115 buff, and 41130A blue spersastain, available from Ferro Corporation, located in Cleveland, Ohio. Additional colorants (e.g., dyes and/or pigments) will be apparent to one skilled in the art.

III. EXAMPLES

Example 1

An exemplary two-part temporary cement composition may be formed by mixing together equal weights of first and second parts as described below:

| Part A: | |
|---|---|
| P-TIDE | 0.5% |
| BisGMA | 10% |

-continued

| | |
|---|---|
| DUDMA | 8% |
| Zinc Oxide | 25% |
| Tween 80 | 55% |
| Fumed silica | 1.5% |
| Part B: | |
| Benzoyl Peroxide | 0.5% |
| HEMA Succinate | 8% |
| ZEODENT 113 | 45% |
| TEGDMA | 8% |
| Water | 1.5% |
| Glycerin | 30% |
| GDMA (phosphated) | 7% |

Example 2

An exemplary two-part temporary cement composition may be formed by mixing together equal weights of first and second parts as described below:

| Part A: | |
|---|---|
| P-TIDE | 0.5% |
| BisGMA | 10% |
| TEGDMA | 8% |
| Zinc Oxide | 10% |
| Tween 80 | 70% |
| Fumed silica | 1.5% |
| Part B: | |
| Benzoyl Peroxide | 0.5% |
| 2-hydroxyethylmethacrylate/phthalic anhydride | 10% |
| ZEODENT 113 | 37% |
| GDMA | 8% |
| HPMA | 10% |
| Water | 4.5% |
| HERCOLYN-D | 30% |

Example 3

An exemplary two-part temporary cement composition was formed by mixing together equal weights of first and second parts as described below:

| Part A: | |
|---|---|
| P-TIDE | 0.5% |
| BisGMA | 34% |
| TEGDMA | 15% |
| Zinc Oxide | 29% |
| ZEODENT 113 | 19% |
| Suncroma yellow iron oxide pigment | 0.075% |
| V-9117 deep tan pigment | 0.05 |
| V-9115 buff pigment | 0.0125 |
| Fumed silica | 2% |
| Part B: | |
| Benzoyl Peroxide | 0.4% |
| HEMA Succinate | 12% |
| GDMA (phosphated) | 2% |
| HPMA | 10% |
| Polybutadiene | 66.57% |
| Water | 0.5% |
| Fumed Silica | 7% |
| 41130A blue spersastain pigment | 0.035% |
| Almond oil flavorant | 1.5% |

The temporary cement composition was tested and found to have a compressive strength of about 17 MPa and a bonding strength of about 0.6 MPa. Compressive strength was measured by placing the mixed two-part composition into a cylindrical mold and allowed to cure. After curing, the sample was removed from the mold and sanded with sand paper to reduce the cylinder to a cylinder having dimensions of 2.15 mm in height and 2.35 mm in diameter. An INSTRON compressive strength measuring device was used to crush the sample so as to test compressive strength. Bonding strength was measured by performing a simulated "crown pull" test. The crown pull test was performed by shaping a human tooth into a conical shape. Using the cement composition to be tested, a corresponding metal simulated "crown" was cemented onto the tooth. The INSTRON device was used to pull the crown off the tooth so as to test bonding strength. The fracturing occurred within the cement composition (i.e., not at the interface between the simulated metal "crown" and the cement. In measuring both compressive and bonding strength, each test was performed multiple times and the results averaged. In addition, each sample was soaked in water for 24 hours before being broken.

Example 4

An exemplary two-part temporary cement composition was formed by mixing together equal weights of first and second parts as described below:

| Part A: | |
|---|---|
| P-TIDE | 0.5% |
| BisGMA | 34% |
| TEGDMA | 15% |
| Zinc Oxide | 29% |
| ZEODENT 113 | 19% |
| Suncroma yellow iron oxide pigment | 0.075% |
| V-9117 deep tan pigment | 0.05 |
| V-9115 buff pigment | 0.0125 |
| Fumed silica | 2% |
| Part B: | |
| Benzoyl Peroxide | 0.4% |
| HEMA Succinate | 12% |
| GDMA (phosphated) | 2% |
| HPMA | 10% |
| Polybutadiene | 56.57% |
| Cetyl Alcohol | 10% |
| Water | 0.5% |
| Fumed Silica | 7% |
| 41130A blue spersastain pigment | 0.035% |
| Almond oil flavorant | 1.5% |

The temporary cement composition was tested and found to have a compressive strength of about 29 MPa and a bonding strength of about 0.8 MPa. In measuring compressive strength and bonding strength, the same methology as described in conjunction with Example 3 was used.

IV. Exemplary Methods of Use

FIG. 1A illustrates an exemplary system 100 including a first syringe 102a and a second syringe 102b in which the two-part composition is contained. First syringe 102a contains first part 104a of the composition, while second syringe 102b contains second part 104b of the composition. As shown, quantities of each part may be dispensed and mixed on the surface of mixing pad 106 (e.g., with a mixing stick or other suitable tool).

Figure 1B:
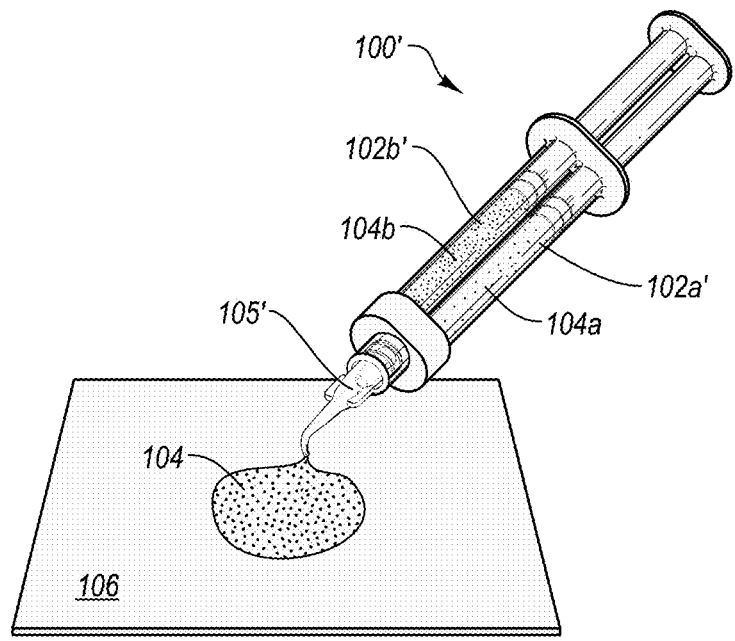

FIG. 1B illustrates an alternative exemplary combination dispensing and mixing system 100' including a first syringe barrel 102a' and a second syringe barrel 102b' which are integrally connected side by side. Such an apparatus may be injection molded. First barrel 102a' contains first part 104a of the composition, while second syringe 102b' contains second part 104b of the composition. As shown, quantities of each part may be dispensed in an already mixed state as composition 104 from mixing and dispensing tip 105' onto pad 106.

Figure 2A:
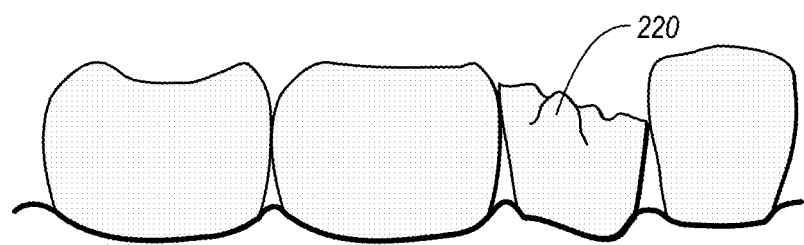
FIG. 2A illustrates a plurality of teeth, one of which is in need of restoration.
Figure 2B:
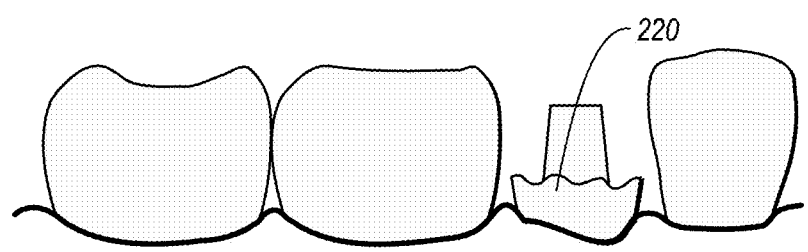
FIG. 2B shows the broken tooth of FIG. 2A having been reduced and the resulting surface prepared in preparation for bonding a provisional dental prosthetic appliance.
Figure 2C:
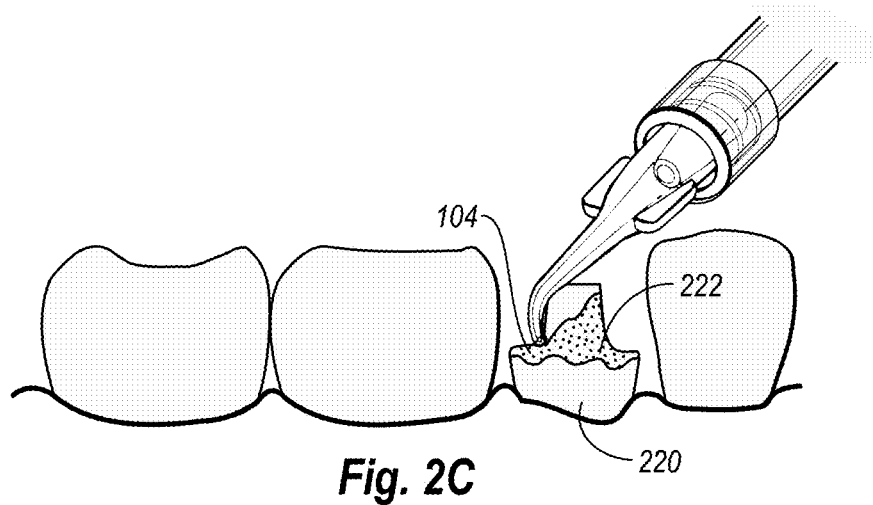
FIG. 2C illustrates an exemplary mixed temporary cement composition being applied to the prepared tooth surface of FIG. 2B.
Figure 2D:
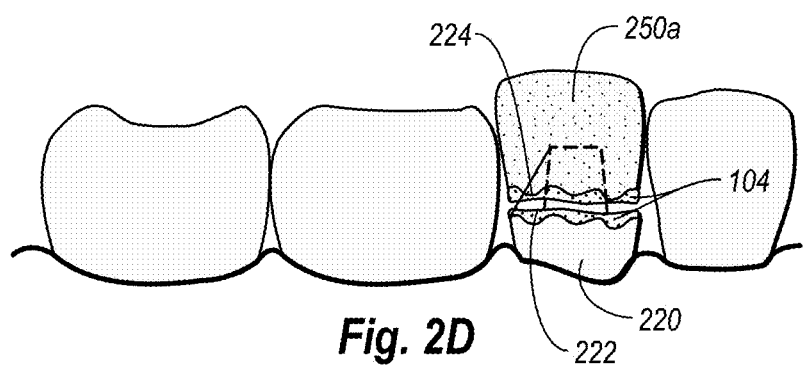
FIG. 2D illustrates a provisional dental prosthetic appliance being positioned for bonding.
Figure 2E:
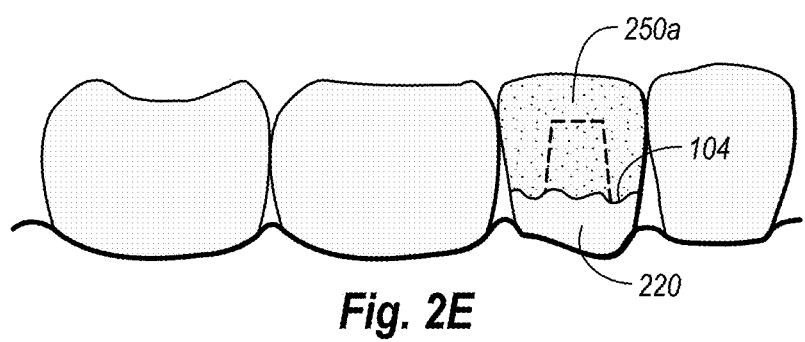
FIG. 2E illustrates the provisional dental appliance bonded to the broken tooth with the inventive temporary cement composition.

FIG. 2A is a perspective view of several of a person's teeth including one broken tooth 220 in need of restoration. As shown in FIG. 2B, the broken tooth 220 may be reduced and prepared as necessary (e.g., insertion of a post and buildup of core material around the post) and the surface may be prepared (e.g., etched and primed) for bonding a provisional dental appliance. As shown in FIGS. 2C-2D, mixed temporary cement composition 104 may be applied to the prepared tooth surface 222 and/or the corresponding surface 224 of provisional appliance 250a. As shown in FIG. 2E, provisional appliance 250a is bonded to tooth substrate 220 with temporary cement 104.

Figure 3A:
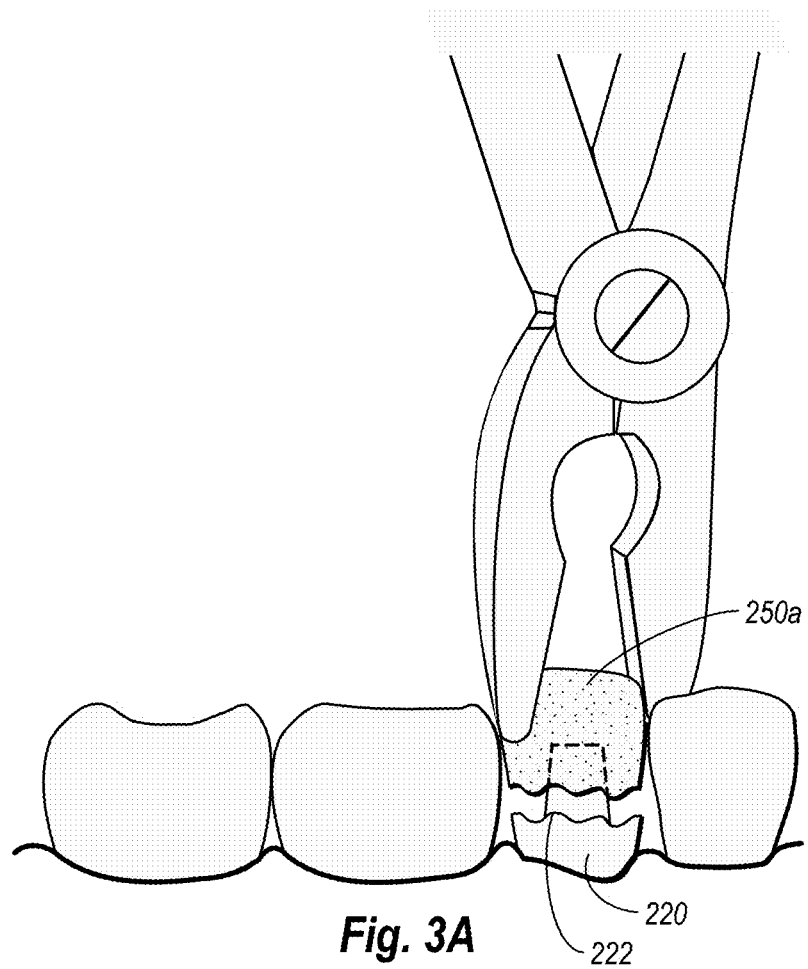
FIG. 3A illustrates the provisional dental appliance being removed from the broken tooth so as to allow placement and bonding of a permanent restoration.
Figure 3B:
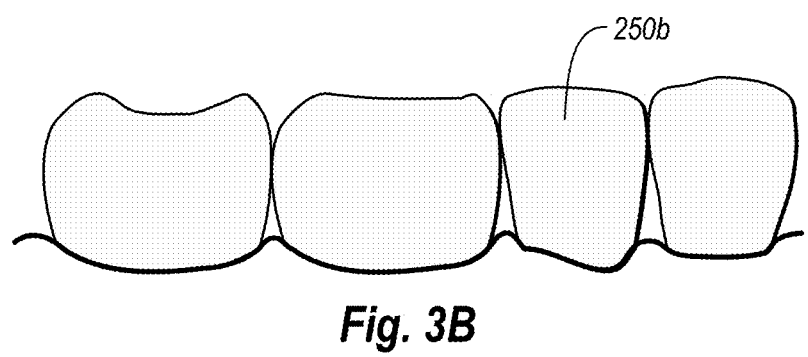
FIG. 3B illustrates the permanent restoration bonded to the broken tooth substrate.

Because of its relatively low bonding strength, temporary cement 104 advantageously allows for easy removal of provisional appliance 250a and replacement with a permanent appliance once the permanent appliance has been prepared and is ready for installation. As shown in FIG. 3A, pliers or other means may be used to pull off provisional appliance 250a. Because of the relatively low bonding strength of temporary cement composition 104, separation easily and cleanly occurs at the bonding interface 222. The permanent appliance 250b may then be bonded using a permanent bonding cement (FIG. 3B).

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A two-part dental cement composition, comprising:
   a first part including zinc oxide;
   a second part including a polymerizable component consisting of a linear structure with at least one acrylate or methacrylate group at one end of the linear structure and a carboxylic acid group at the other end of the linear structure; and
   a plasticizer in at least one of the first or second parts.

2. The two-part dental cement composition of claim 1, wherein the first part further includes an amine activator.

3. The two-part dental cement composition of claim 2, wherein the amine activator comprises a tertiary amine.

4. The two-part dental cement composition of claim 1, wherein the plasticizer comprises at least one of glycerin, hydrogenated methyl ester of rosin, or an aliphatic hydrocarbon.

5. The two-part dental cement composition of claim 1, wherein the plasticizer comprises at least one of polybutadiene, cetyl alcohol, or polysorbate.

6. The two-part dental cement composition of claim 1, wherein the plasticizer comprises between about 25% by weight and 60% by weight of the two-part dental cement composition.

7. The two-part dental cement composition of claim 1, wherein the plasticizer comprises between about 30% by weight and 40% by weight of the two-part dental cement composition.

8. The two-part dental cement composition of claim 1, wherein at least one of the first or second parts further comprises an unreactive filler.

9. The two-part dental cement composition of claim 8, wherein the plasticizer and the unreactive filler comprises at least 35% by weight of the two-part cement composition.

10. The two-part dental cement composition of claim 1, wherein at least one of the first part or the second part comprises a cross-linking polymerizable component comprises at least one of a diacrylate or a dimethacrylate.

11. The two-part dental cement composition of claim 1, wherein the polymerizable component has a single acrylate or methacrylate group at the one end and a single carboxylic acid group at the other end.

12. The two-part dental cement composition of claim 1, wherein the polymerizable component is mono-2-(methacryloyloxy)ethyl succinate.

13. A kit for bonding a provisional dental prosthetic appliance to a tooth comprising:
   a first syringe having a first part therein, the first part comprising zinc oxide;
   a second syringe having a second part therein, the second part comprising a polymerizable component consisting of a linear structure with at least one acrylate or methacrylate group at one end of the linear structure and a carboxylic acid group at the other end of the linear structure; and
   a plasticizer in at least one of the first or second parts.

14. The kit of claim 13, wherein the first syringe and the second syringe are connected side-by-side.

15. The kit of claim 13, further comprising at least one mixing and dispensing tip configured to be disposed on an end of first and second syringes.

16. A two-part dental cement composition, comprising:
   a first part including at least one cross-linkable polymerizable component, a tertiary amine activator, and zinc oxide;
   a second part including an initiator, water, and a polymerizable component having a linear structure with only two ends and including at least one acrylate or methacrylate group at one of the two ends of the linear structure and a carboxylic acid group at the other of the two ends of the linear structure; and
   a plasticizer in at least one of the first or second parts.

17. The two-part dental cement composition of claim 16, wherein the second part further includes a butylated hydroxytoluene (BHT) inhibitor.

18. The two-part dental cement composition of claim 16, wherein the polymerizable component comprises mono-2-(methacryloyloxy)ethyl succinate.

19. The two-part dental cement composition of claim 16, wherein the at least one cross-linkable polymerizable component comprises at least one diacrylate or dimethacrylate.

20. The two-part dental cement composition of claim 16, wherein the plasticizer comprises at least one of glycerin, hydrogenated methyl ester of rosin, or an aliphatic hydrocarbon.

21. The two-part dental cement composition of claim 16, the polymerizable component having a structure including the acrylate or methacrylate group at one end and the carboxylic acid group at another end.

22. The two-part dental cement composition of claim 16, wherein the polymerizable component comprises at least one of mono-2-(methacryloyloxy)ethyl succinate or 2-hydroxyethylmethacrylate/phthalic anhydride.

* * * * *

UNITED STATES PATENT AND TRADEMARK OFFICE
CERTIFICATE OF CORRECTION

| | | |
|---|---|---|
| PATENT NO. | : 10,369,085 B2 | Page 1 of 1 |
| APPLICATION NO. | : 15/883383 | |
| DATED | : August 6, 2019 | |
| INVENTOR(S) | : Kennard et al. | |

It is certified that error appears in the above-identified patent and that said Letters Patent is hereby corrected as shown below:

In the Specification

Column 2
Line 17, change "40%)" to –40%–

Column 5
Line 57, change "more" to –most–

Signed and Sealed this
Fourth Day of February, 2020

Andrei Iancu
*Director of the United States Patent and Trademark Office*